United States Patent [19]
Nanjo et al.

[11] Patent Number: 5,166,164
[45] Date of Patent: Nov. 24, 1992

[54] NITROGUANIDINE COMPOUNDS USEFUL AS INSECTICIDES

[75] Inventors: Katsumi Nanjo; Kiyoshi Takasuka; Shigenori Segami, all of Tokorozawa; Akinori Kariya, Higashimurayama, all of Japan

[73] Assignee: Agro-Kanesho Co., Ltd., Tokyo, Japan

[21] Appl. No.: 596,039

[22] Filed: Oct. 11, 1990

[30] Foreign Application Priority Data

Oct. 24, 1989 [JP] Japan .................. 1-276633
Dec. 19, 1989 [JP] Japan .................. 1-328888

[51] Int. Cl.$^5$ ................. C07D 213/61; C07D 277/32; A01N 47/44
[52] U.S. Cl. .................. 514/357; 514/365; 546/332; 548/205
[58] Field of Search .............. 546/332; 548/205; 514/357, 365

[56] References Cited

FOREIGN PATENT DOCUMENTS 0302389 2/1989 European Pat. Off. ............ 546/329
0375907 7/1990 European Pat. Off. ............ 546/329

Primary Examiner—C. Warren Ivy
Assistant Examiner—Zinna Northington Davis
Attorney, Agent, or Firm—Oblon, Spivak, McClelland, Maier & Neustadt

[57] ABSTRACT

Insecticides which are improved over the conventional insectides are provided by the use of a nitroguanidine compound represented by the following general formula (I):

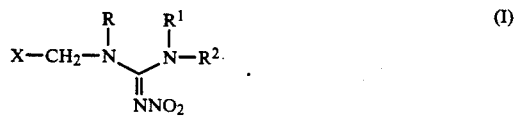

wherein R stands for hyydrogen or methyl; $R^1$ and $R^2$ are the same or different, and stand for hydrogen or methyl; and X stands for a group indicated by

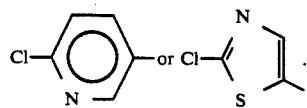

The insecticides provided by this invention are extremely active for controlling various harmful insects and yet are low in toxicity to warm-blooded animals, fishes and Crustacea, the remaining quantity thereof after their use is small, and they do not produce phytotoxicity in various plants.

20 Claims, No Drawings

NITROGUANIDINE COMPOUNDS USEFUL AS INSECTICIDES

BACKGROUND OF THE INVENTION

1. Field of the Invention

The present invention relates to nitroguanidine compounds, a process for preparing the same, and insecticides containing the same as active ingredients. The nitroguanidine compounds provided by this invention are represented by the following general formula (I):

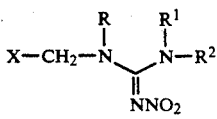

wherein R stands for hydrogen or methyl; $R^1$ and $R^2$ are the same or different, and stand for hydrogen, or methyl; and X stands for a group indicated by

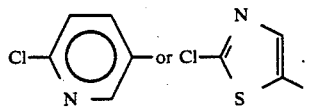

2. Prior Art

A variety of chemicals have been developed and used as insecticides for controlling harmful insects. Representative examples of such chemicals are organic phosphorous compounds carbamate compounds and synthetic pyrethroids. However, by the repeated use of these insecticides, many harmful insects have acquired resistance to these chemicals, thus making it difficult to control such insects. On the other hand, although some conventional insecticides have high insecticidal activity, they might cause environmental pollution problems either due to their high toxicity to warm-blooded animals or fishes and Crustacea or due to their remaining in the environment in large amounts for a long time after use, thus putting the ecological system out of order. Accordingly, there is a demand for the development of novel insecticides which more effectively control harmful insects, which have acquired resistance to conventional chemicals, and yet are low in toxicity not only to warm-blooded animals but also fishes and Crustacea. There is also a demand for novel insecticides which remain in plants and soils in decreased amounts after their use, and do not produce phytotoxicity in various plants.

OBJECTS AND SUMMARY OF THE INVENTION

An object of this invention is to provide novel compounds which (1) more effectively control harmful insects that have acquired resistance to conventional chemicals, (2) are low in toxicity not only to warm-blooded animals but also fishes and Crustacea and (3) remain in decreased amounts in plants and soils after their use. Lastly, such novel compounds do not produce phytotoxicity in various plants.

Another object of this invention is to provide a process for preparing such compounds.

A further object of this invention is to provide improved insecticides which (1) more effectively control harmful insects having resistance to conventional insecticides, (2) are low in toxicity not only to warm-blooded animals but also fishes and Crustacea, and (3) remain in decreased amounts in plants and soils after their use. Lastly, such improved insecticides do not produce phytotoxicity in various plants.

Through research toward the development of various novel nitroguanidine compounds, we have found that the nitroguanidine compounds represented by the following general formula (I):

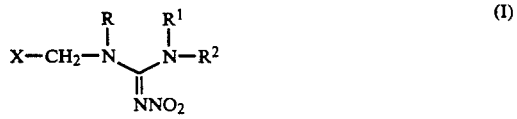

wherein R stands for hydrogen or methyl; $R^1$ and $R^2$ are the same or different, and stand for hydrogen or methyl; and X stands for a group indicated by

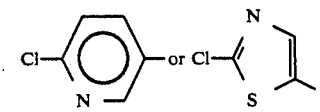

can be used as extremely powerful insecticides which exhibit rapid effects. The present invention has been developed on the basis of this finding.

Further objects, features and advantages of the present invention will become apparent from the Detailed Description of the Preferred Embodiments which follows, when considered together with the illustrative examples.

DETAILED DESCRIPTION OF THE PREFERRED EMBODIMENTS

The compounds of this invention represented by the general formula (I) are novel compounds which have not been described in any prior publication and were synthesized by us for the first time. These compounds may be prepared by the processes described below.

Preparation Process (a)

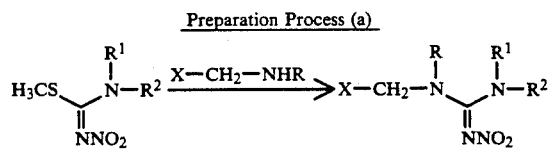

wherein R stands for hydrogen or methyl; $R^1$ and $R^2$ are the same or different, and stand for hydrogen or methyl; and X stands for a group indicated by

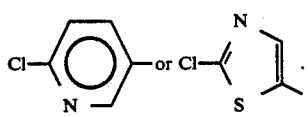

In the preparation process (a), as indicated by the reaction formula set forth above, the compounds of this invention may be readily prepared by reacting, with or without solvents a compound represented by the general formula (II):

(II)

wherein R stands for hydrogen or methyl, and X stands for a group indicated by

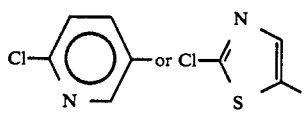

with a compound represented by the general formula (III):

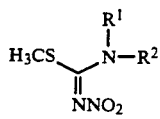     (III)

wherein $R^1$ and $R^2$ are the same or different, and stand for hydrogen or methyl.

Examples of the suitable solvents which may be used in this reaction are: ethers such as diethyl ether and tetrahydrofuran; alcohols such as methanol and ethanol; acetonitrile; aromatic hydrocarbons; chlorinated hydrocarbons; DMF; and DMSO. These solvents may be used alone or in combination. Particularly preferable solvents are alcohols such as methanol and ethanol.

The reaction temperature may be freely set within a range of from room temperature to 150° C., preferably from room temperature to 80° C.

Preparation Process (b)

This process may be adopted when the groups R, $R^1$ and $R^2$ of general formula (I) are in a certain special interrelation.

More particularly, according to this process, the compounds of this invention may be readily prepared by reacting a compound represented by the general formula (IV):

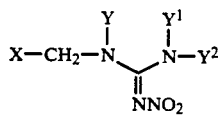     (IV)

wherein Y, $Y^1$ and $Y^2$ are the same or different, and stand for hydrogen or methyl provided that at least one of them is hydrogen; and X stands for a group indicated by

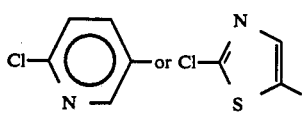

with a compound (V) represented by the general formula (v):

Ch$_3$Z     (V)

wherein Z stands for halogen; in the presence of a basic material, generally by using the compound (v) in a molar ratio of from 1 to 3.3 mols per 1 mol of the compound (IV), whereby a compound of this invention represented by the following formula (I') is prepared.

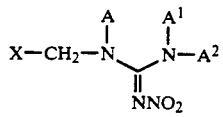     (I')

wherein A, $A^1$ and $A^3$ are the same or different, and stand for hydrogen or methyl provided that at least one of them is methyl, and X stands for a group indicated by

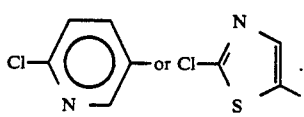

Examples of solvent which may be used in this reaction are: ethers such as diethyl ether and tetrahydrofuran; acetonitrile; aromatic hydrocarbons; chlorinated hydrocarbons; DMF; and DMSO. These solvents may be used alone or in combination. Particularly preferable solvents are DMF and DMSO. Compounds which may be used as the basic materials are, for example, inorganic bases such as sodium hydride, sodium hydroxide and potassium carbonate, and organic bases such as DBU. These bases may be used in a molar ratio of from 1 to 3.3 per 1 mol of the compound (IV). The reaction temperature may be set within a range of from —(minus) 20° C. to 100° C., preferably from —(minus) 10° C. to 60° C.

It should be noted again that the compounds of this invention are novel compounds. Typical compounds (I) of the present invention prepared by the above processes are set forth in the following Table 1.

TABLE 1

$$X-CH_2-N\begin{array}{c}R\\|\end{array}\begin{array}{c}R^1\\|\end{array}N-R^2$$
$$\|$$
$$NNO_2$$
(I)

| Compound No. | R | $R^1$ | $R^2$ | Melting Point |
|---|---|---|---|---|
| 1 | CH$_3$ | H | H | Decomposed at 158.0° C. |
| 2 | CH$_3$ | CH$_3$ | CH$_3$ | 99.0 to 100.0° C. |
| 3 | H | CH$_3$ | H | 152.5 to 153.5° C. |
| 4 | H | H | H | 198.0 to 199.0° C. |
| 5 | CH$_3$ | CH$_3$ | H | 130.0 to 132.0° C. |
| 6 | CH$_3$ | H | H | 116.0 to 117.0° C. |
| 7 | CH$_3$ | CH$_3$ | CH$_3$ | 101.0 to 102.0° C. |
| 8 | H | CH$_3$ | H | 151.0 to 153.0° C. |
| 9 | H | H | H | 160.0 to 162.0° C. |

Note:
The compounds denoted by 1 to 5 are compounds represented by the general formula (I) wherein X is Cl—[pyridyl]; and the compounds denoted by 6 to 9 are compounds represented by the general formula (I) wherein X is Cl—[thiazolyl]

An effective amount of any of the compounds of this invention may be applied directly as an insecticide or may be formulated by conventional technology in the form of an emulsion, a wettable powder, a dust, a granule or in a flowable form, and then applied as a formulated product. A liquid or solid carrier may be used for preparing a formulated product containing one or more of the compounds of this invention. Liquid carriers which may be used for this purpose include, for example, organic solvents, and conveniently used are xylene, chlorobenzene, methylnaphthalene, cyclohexanone, isophorone, alcohols, dimethylformamide and N-methylpyrrolidone. Examples of solid carriers include kaoline, talc, bentonite, diatomaceous earth and clay, and synthetic compounds such as alumina, zeolite and silicates may also be used. In preparation of the formulated products, various adjuvants, such as emulsifiers, dispersants, spreaders, wetting agents and penetrating agents, may be used for providing the products with the desired properties of emulsification, dispersion, suspension and penetration.

The compounds of this invention, which are represented by the general formula (I) set forth above, have strong insecticidal activity against various harmful insects, including Hemiptera, Lepidoptera, Coleoptera, Diptera, Orthoptera and Isoptera, and yet are low in toxicity to human beings and animals and do not produce phytotoxicity in various plants, and thus can be practically used as superior insecticides.

Examples of harmful insects which may be effectively controlled by the compounds of this invention are as follows:

Hemiptera such as *Nilaparvata lugens, Laodelphax striatellus, Nephotettix cincticeps, Pseudococcus comstocki, Unaspis yanonensis, Myzus persicae, Aphis gossypii, Lipaphis erysimi, Stephanitis nashi, Scotinophara lurida* and *Trialeurodes vaporariorus;* such as *Pieris rapae, Spodoptera litura, Mamestra brassicae, Chilo suppressalis, Plutera xylostella, Adoxophyes orana, Agrotis fucosa, Cnaphalocrocis medinalis* and *Ostrinia furnacalis;* Coleoptera such as *Henosepilachna vigintioctopunctata, Aulacophora femoralis, Phyllotreta striolata, Lissorhoptrus oryzophilus, Sitophilus zeamais* and *Anomala rufocuprea.* Diptera such as *Musca domestica, Hylemia platura, Culex pipiens;* Orthoptera such as *Gryllotalpa africana, Blatella germanica* and *Locusta migratoria;* and Isoptera such as *Coptotermes formosanus* and *Reticulitermes speratus.*

The present invention will now further be explained by way of the following non-limiting examples.

Examples

The processes for the preparation of the compounds of this invention are described in detail by referring to some Synthesis Examples.

Synthesis Example 1

Synthesis of
N-[(6-chloro-3-pyridinyl)methyl]-N-methyl-N'-nitroguanidine

A mixture of 13.8 g of 6-chloro-N-methyl-3-pyridinemethanamine, 10.8 g of S-methyl-N-nitroisothiourea and 60 ml of ethanol was heated at 50° C. with stirring for 2 hours and then refluxed for additional 5 hours. After cooling, the separated crystal was collected by filtration, washed with a small amount of ethanol, and dried to obtain 14.7 g of the title compound. This compound is No.1 in Table 1. m.p.: 158.0° C. (Decomposed).

Synthesis Example 2

Synthesis of
N-[(6-chloro-3-pyridinyl)methyl]-N,N',N'-trimethyl-N'-nitroguanidine To a mixture of 0.21 g of sodium hydride (60% oily) and 4 ml of N,N-dimethylformamide, 1.22 g of N-[(6-chloro-3-pyridinyl) methyl]-N-methyl-N'-nitroguanidine was added in portions with stirring under cooling with ice. Then, the mixture was stirred at room temperature. This was followed by one-hour additional stirring, and thereafter 0.74 g of methyl iodide was added dropwise. After stirring over night, the reaction mixture was poured into ice-water and the insoluble substance was filtered off. The filtrate was extracted with dichloromethane. The dichloromethane layer was washed with water, dried, concentrated. The residue was purified by silica gel column chromatography (Solvent: Chloroform/Methanol=50/1) to obtain 0.31 g of the title compound. This compound is No. 2 in Table 1. m.p. 99.0°–100.0° C.

Synthesis Example 3

Synthesis of
N-[(2-chloro-5-thiazolyl)methyl]-N-methyl-N'-nitroguanidine

A mixture of 1.50 g of 2-chloro-N-methyl-5-thiazolemethanamine, 1.13 g of S-methyl-N-nitroisothiourea and 6 ml of ethanol was heated under reflux for 6 hours. After cooling, the reaction mixture was concentrated under reduced pressure and the residue was purified by silica gel column chromatography (Solvent: Chloroform/Methanol=20/1) to obtain 1.00 g of the title compound as crystals. This compound is No. 6 in Table 1. m.p.: 116.0°–117.0° C.

Synthesis Example 4

Synthesis of
N-[(2-chloro-5-thiazolyl)methyl]-N,N',N'-trimethyl-N''-nitroguanidine 0.15 g of sodium hydride (60% oily) was added in portion to a mixture of 0.83 g of N-[(2-chloro-5-thiazolyl)methyl]-N-methyl-N'-nitroguanidine and 10 ml of N,N-dimethylform with stirring under cooling with ice-water. After the addition, the reaction mixture was stirred for additional 1.5 hours. 0.54 g of methyl iodide was added dropwise to the reaction mixture. After the temperature of the reaction mixture was returned to room temperature, it was stirred over night. The reaction mixture was poured into ice water, and then extracted with chloroform. The chloroform layer was washed with water, dried, concentrated, and then N-methyl-N'silica gel column chromatography (Solvent: Chloroform/Methanol 50/1 to 10/1) to obtain 0.15 g of the title compound as crystals. This compound is No. 7 in Table 1. m.p.: 101.0°–102.0° C.

Synthesis Example 5

Synthesis of N-[(2-chloro-5-thiazolyl)methyl]-N'-methyl-N''-nitroguanidine

A mixture of 0.48 g of 2-chloro-5-thiazolemethanamine, 0.31 g of S-methyl-N-methyl-N'-nitroisothiourea prepared by the method described in the Journal of Medical Chemistry., 1977, Vol. 20, No. 7, P. 905 and 3 ml of ethanol was heated under reflux for 6 hours. After cooling, the reaction mixture was concentrated under reduced pressure, and the residue was purified by silica gel column chromatography (Solvent: Chloroform/Methanol =20/1) to obtain 0.37 g of the title compound as crystals. This compound is No. 8 in Table 1. m.p.: 151.0°–153.0° C.

Synthesis Example 6

Synthesis of N-[(2-chloro-5-thiazolyl)methyl]-N'-nitroguanidine

A mixture of 0.35 g of 2-chloro-5-thiazolemethanamine, 0.31 g of S-methyl-N-nitroisothiourea and 3 ml of ethanol was heated under reflux for 6 hours. After cooling, the separated crystals were collected by filtration, washed with a small amount of ethanol, and then recrystalized from ethanol to obtain 0.42 g of the title compound as crystals. This compound is No. 9 in Table 1. m.p.: 160.0°–162.0° C.

Some specific Formulation Examples are shown below. However, it is noted that the carriers, surfactants and other additives which may be used in formulation of the insecticides according to this invention are not limited by the following Formulation Examples. In the following Formulation Examples, "part" stands for "part by weight".

Formulation Example 1

32.5 Parts of the Compound No. 1 in Table 1, 3 parts of lignin sulfonic acid, 4 parts of polyoxyethylene alkylphenyl ether, 2 parts of silicon dioxide hydrate and 58.5 parts of clay are well mixed while being powdered to obtain a wettable powder.

Formulation Example 2

5.4 Parts of the Compound No. 2 in Table 1, 2 parts of silicon dioxide hydrate and 92.6 parts of talc are well mixed while being powdered to obtain a dust.

Formulation Example 3

5.4 Parts of the Compound No. 8 in Table 1, 3 parts of lignin sulfonate, 1 part of sodium dodecylsulfonate, 30 parts of bentonite and 60.6 parts of clay are well mixed while being powdered. The mixture is then kneaded with water, granulated and dried to obtain granules.

The insecticidal effects of the compounds of this invention are shown by referring to some Test Examples.

Test Example 1

Five rice seedlings having a height of 7 cm were dipped, for 10 seconds, into aqueous dilutions of wettable powder each containing a predetermined concentration of each sample compound, prepared in accordance with the procedure as described in Formulation Example 1. After air drying, the roots of the five rice seedlings were wrapped with sanitary cotton dampened with water, and placed in a glass cylinder having a diameter of 3 cm and a height of 20 cm. Ten second instar larvae of a green rice leafhopper which had acquired resistance to chemicals were released into each glass cylinder. The cylinder was allowed to stand in a room maintained at 26° C. The mortality of the larvae was examined 48 hours after treatment. The results are shown in Table 2.

TABLE 2

| Compound No. | Mortality (%), 500 ppm |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| Comparative Compound | 70 |

Note:
The comparative compound set forth in Table 2 is Sumithion (Trade Name), represented by the following formula.

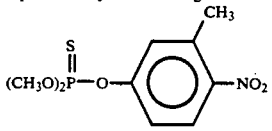

Test Example 2

Five rice seedlings having a height of 7 cm were dipped, for 10 seconds, into aqueous dilutions of wettable powder each containing a predetermined concentration of each sample compound, prepared in accordance with the procedure as described in Formulation Example 1. After air drying, the roots of the five rice seedlings were wrapped with sanitary cotton dampened with water, and placed in a glass cylinder having a diameter of 3 cm and a height of 20 cm. Ten second instar larvae of a brown rice planthopper which had acquired resistance to chemicals were released into each glass cylinder. The cylinder was allowed to stand in a room maintained at 26° C. The mortality of the larvae was examined 48 hours after treatment. The results are shown in Table 3.

TABLE 3

| Compound No. | Mortality (%), 500 ppm |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| Comparative Compound | 65 |

Note:
The comparative compound set forth in Table 3 is the same as that in Table 2.

As will be apparent from the foregoing, the compounds of this invention are extremely active for controlling various harmful insects and yet are low in toxicity to warm-blooded animals, fishes and Crustacea, the remaining quantity thereof after their use is small, and they do not produce phytotoxicity in various plants.

We claim:

1. A nitroguanidine compound represented by the following general formula (I):

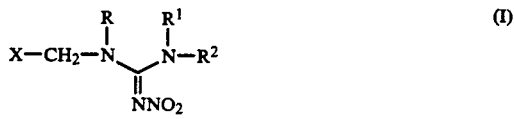

wherein R stands for hydrogen or methyl; R¹ and R² are the same or different, and stand for hydrogen or methyl; and X stands for a group indicated by

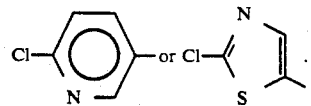

2. The nitroguanidine compound according to claim 1 which is N-[(6-chloro-3-pyridinyl)methyl]-N-methyl-N'-nitroguanidine.

3. The nitroguanidine compound according to claim 1 which is N-[(6-chloro-3-pyridinyl)methyl]-N,N'-trimethyl-N''-nitroguanidine.

4. The nitroguanidine compound according to claim 1 which is N-[(6-chloro-3pyridinyl)methyl]-N'-methyl-N''-nitroguanidine.

5. The nitroguanidine compound according to claim 1 which is N-[(6-chloro-3-pyridinyl)methyl]-N'-nitroguanidine.

6. The nitroguanidine compound according to claim 1 which is N-[(6-chloro-3-pyridinyl)methyl]-N,N'-dimethyl-N''-nitroguanidine.

7. The nitroguanidine compound according to claim 1 which is N-[(2-chloro-5-thiazolyl)methyl]-N-methyl-N'-nitroguanidine.

8. The nitroguanidine compound according to claim 1 which is N-[(2-chloro-5-thiazolyl)methyl]-N,N',N'-trimethyl-N''-nitroguanidine.

9. The nitroguanidine compound according to claim 1 which is N-[(2-chloro-5-thiazolyl)methyl]-N'-methyl-N''-nitroguanidine.

10. The nitroguanidine compound according to claim 1 which is N-[(2-chloro-5-thiazolyl)methyl]-N'-nitroguanidine.

11. An insecticidal composition containing a suitable carrier and an insecticidally effective amount of a nitroguanidine compound represented by the formula (I):

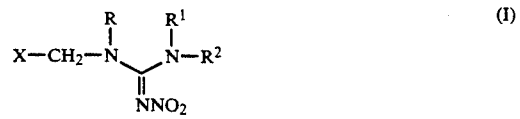

wherein R stands for hydrogen or methyl; R¹ and R² are the same or different, and stand for hydrogen or methyl; and X stands for a group indicated by

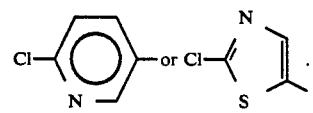

12. The insecticidal composition according to claim 11 wherein the compound is N-[(6-chloro-3-pyridinyl)-methyl]-N-methyl-N'-nitroguanidine.

13. The insecticidal composition according to claim 11 wherein the compound is N-[(6-chloro-3-pyridinyl)-methyl]-N,N',N'-trimethyl-N''-nitroguanidine.

14. The insecticidal composition according to claim 11 wherein the compound is N-[(6-chloro-3-pyridinyl)-methyl]-N'-methyl-N''-nitroguanidine.

15. The insecticidal composition according to claim 11 wherein the compound is N-[(6-chloro-3-pyridinyl)-methyl]-N'-nitroguanidine.

16. The insecticidal composition according to claim 11 wherein the compound is N-[(6-chloro-3-pyridinyl)-methyl]-N,N'-dimethyl-N''-nitroguanidine.

17. The insecticidal composition according to claim 11 wherein the compound is N-[(2-chloro-5-thiazolyl)-methyl]-N-methyl-N'-nitroguanidine.

18. The insecticidal composition according to claim 11 wherein the compound is N-[(2-chloro-5-thiazolyl)]-N,N',N'-trimethyl-N''-nitroguanidine.

19. The insecticidal composition according to claim 11 wherein the compound is N-[(2-chloro-5-thiazolyl)-methyl]-N'-methyl-N''-nitroguanidine.

20. The insecticidal composition according to claim 11 wherein the compound is N-[(2-chloro-5-thiazolyl)-methyl]-N'-nitroguanidine.

* * * * *